US012269864B2

(12) United States Patent
Conticello et al.

(10) Patent No.: US 12,269,864 B2
(45) Date of Patent: Apr. 8, 2025

(54) SELF-ASSEMBLING COLLAGEN-LIKE POLYPEPTIDES FOR APPLICATIONS AND USES RELATED THERETO

(71) Applicant: Emory University, Atlanta, GA (US)

(72) Inventors: Vincent Conticello, Avondale Estates, GA (US); Andrea Merg, Atlanta, GA (US); Gavin Touponse, Fort Worth, TX (US)

(73) Assignee: Emory University, Atlanta, GA (US)

( * ) Notice: Subject to any disclaimer, the term of this patent is extended or adjusted under 35 U.S.C. 154(b) by 90 days.

(21) Appl. No.: 17/140,449

(22) Filed: Jan. 4, 2021

(65) Prior Publication Data

US 2021/0206835 A1    Jul. 8, 2021

Related U.S. Application Data

(60) Provisional application No. 62/957,061, filed on Jan. 3, 2020.

(51) Int. Cl.
 C07K 14/78    (2006.01)
(52) U.S. Cl.
 CPC .......... C07K 14/78 (2013.01); *C07K 2319/00* (2013.01)
(58) Field of Classification Search
 None
 See application file for complete search history.

(56) References Cited

U.S. PATENT DOCUMENTS 7,838,491 B2    11/2010 Stupp
9,725,499 B2 *  8/2017 Conticello ............. C07K 14/78

FOREIGN PATENT DOCUMENTS

WO    2016123570    8/2016
WO    2018106273    6/2018

OTHER PUBLICATIONS

Jiang & Conticello et al. (Emory University, Instant Assignee). Structurally Defined Nanoscale Sheets from Self-Assembly of Collagen-Mimetic Peptides. Journal of the American Chemical Society (2014), 136(11), 4300-4308.*
Merg et al. Asymmetry Enables pH-Dependent Formation Interconversion of Collagen Tubes and Sheets. Journal of the American Chemical Society (2020), 142(47), 19956-19968.].*
Conticello V.P., Controlled fabrication of peptide-based nanosheets, American Chemical Society, National Meeting & Exposition, 2019, 1:35 PMSE 100.
Conticello V.P., Rational design of helical nanotubes, American Chemical Society, National Meeting & Exposition, 2019, 3:25 PMSE 307.
Dehsorkhi et al. Self-assembling amphiphilic peptides, J Pept Sci, 2014, 20: 453-467.
Egelman et al. Structural Plasticity of Helical Nanotubes Based on Coiled-Coil Assemblies, Structure, 2015, 23, 280-289.
Fan et al. Peptide Self-Assembled Nanostructures for Drug Delivery Applications, Hindawi, Journal of Nanomaterials vol. 2017, Article ID 4562474, 16 pages.
Habibi et al. Self-assembled peptide-based nanostructures: Smart nanomaterials toward targeted drug delivery, Nano Today, 2016, 11(1): 41-60.
Hartherink et al. Self-Assembly and Mineralization of Peptide-Amphiphile Nanofibers, Science, 2001, 294(5547):1684-8.
Huges et al. Design of peptide nanotubes from tandem repeat protein modules, American Chemical Society, National Meeting & Exposition, 2019, 1:15 PMSE 335.
Jiang et al. Structurally Defined Nanoscale Sheets from Self-Assembly of Collagen-Mimetic Peptides, J Am Chem Soc, 2014, 136, 4300-4308.
Jiang et al. Structurally Homogeneous Nanosheets from Self-Assembly of a Collagen-Mimetic Peptide, Angew Chem Int Ed, 2014, 53, 8367-8371.
Jiang et al. Rational Design of Multilayer Collagen Nanosheets with Compositional and Structural Control, J Am Chem Soc, 2015, 137, 7793-7802.
Merg et al. 2D Crystal Engineering of Nanosheets Assembled from Helical Peptide Building Blocks, Angew Chem Int Ed, 2019, 58, 13507-13512.
Merg et al. Shape-Shifting Peptide Nanomaterials: Surface Asymmetry Enables pH-Dependent Formation and Interconversion of Collagen Tubes and Sheets, J Am Chem Soc, 2020, 142, 19956-19968.
Nutariya et al. Model electrode study of Ru@Pt core-shell nanosheet catalysts: Pure two-dimensional growth via surface limited redox replacement, Electrochimica Acta, (2018) 283, 826-833.
Paramonov et al. Synthesis of Collagen-like Peptide Polymers by Native Chemical Ligation, Macromolecules 2005, 38, 7555-7561.
Parmar et al. Dissecting Electrostatic Contributions to Folding and Self-Assembly Using Designed Multicomponent Peptide Systems, J Am Chem Soc, 2016, 138, 4362-4367.
Perez et al. The Powerful Functions of Peptide-Based Bioactive Matrices for Regenerative Medicine, Ann Biomed Eng, 2015, 43(3):501-14.
Rele et al. D-Periodic Collagen-Mimetic Microfibers, J Am Chem Soc, 2007, 129, 14780-14787.
Touponse, The Design and Assembly of 1D and 2D Multicomponent Collagen Mimetic Peptide Systems, Thesis, Bachelor of Sciences with Honors, Department of Chemistry, 2019.
Touponse et al. Rational design and assembly of macroporous nanotubes derived from collagen-mimetic peptides, American Chemical Society, National Meeting & Exposition, 2019, PMSE 390.

(Continued)

*Primary Examiner* — Maury A Audet
(74) *Attorney, Agent, or Firm* — Emory Patent Group (57) ABSTRACT

This disclosure relates to collagen-like polypeptides and materials containing the same and uses in biomedical applications. In certain embodiments, this disclosure contemplates that collagen-like polypeptides and materials containing the same are functionalized with proteins or small molecules to create useful scaffolds for drug delivery or testing. In certain embodiments, collagen-like polypeptides and materials containing the same are used in cardiac patches, cosmetic surgery, bone grafts, tissue regeneration, and wound healing.

2 Claims, 8 Drawing Sheets

Specification includes a Sequence Listing.

(56) References Cited

OTHER PUBLICATIONS

Umashankara et al. Two prolines with a difference: contrasting stereoelectronic effects of 4R/S-aminoproline on triplex stability in collagen peptides [Pro(X)-Pro(Y)-Gly]n, Chem Commun, 2003, 2606-2607.

Yan et al. Three-Dimensional Crystalline/Amorphous Co/Co3O4 Core/Shell Nanosheets as Efficient Electrocatalysts for the Hydrogen Evolution Reaction, Nano Lett, 2015, 15(9):6015-21.

Zhao et al. Designer Self-Assembling Peptide Materials, Macromol Biosci, 2007, 7, 13-22.

* cited by examiner

CMPs

R4P6: (Pro-Arg-Gly)$_4$-(Pro-Hyp-Gly)$_6$  SEQ ID NO: 1

R6P6: (Pro-Arg-Gly)$_6$-(Pro-Hyp-Gly)$_6$  SEQ ID NO: 3

SEQUENCE LISTING

```
<160> NUMBER OF SEQ ID NOS: 3

<210> SEQ ID NO 1
<211> LENGTH: 31
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(31)
<223> OTHER INFORMATION: X is hydroxyproline

<400> SEQUENCE: 1

Pro Arg Gly Pro Arg Gly Pro Arg Gly Pro Arg Gly Pro Pro Xaa Gly
1               5                   10                  15

Pro Xaa Gly Pro Xaa Gly Pro Xaa Gly Pro Xaa Gly Pro Xaa Gly
            20                  25                  30
```

```
<210> SEQ ID NO 2
<211> LENGTH: 30
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(30)
<223> OTHER INFORMATION: X is hydroxyproline

<400> SEQUENCE: 2

Pro Xaa Gly Pro Xaa Gly Pro Xaa Gly Pro Xaa Gly Pro Xaa Gly Pro
1               5                   10                  15

Xaa Gly Glu Xaa Gly Glu Xaa Gly Glu Xaa Gly Glu Xaa Gly
            20                  25                  30

<210> SEQ ID NO 3
<211> LENGTH: 36
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(36)
<223> OTHER INFORMATION: X is hydroxyproline

<400> SEQUENCE: 3

Pro Arg Gly Pro Arg Gly Pro Arg Gly Pro Arg Gly Pro Arg Gly Pro
1               5                   10                  15

Arg Gly Pro Xaa Gly Pro Xaa Gly Pro Xaa Gly Pro Xaa Gly Pro Xaa
            20                  25                  30

Gly Pro Xaa Gly
        35
```

SELF-ASSEMBLING COLLAGEN-LIKE POLYPEPTIDES FOR APPLICATIONS AND USES RELATED THERETO

CROSS-REFERENCE TO RELATED APPLICATIONS

This application claims the benefit of U.S. Provisional Application No. 62/957,061 filed Jan. 3, 2020. The entirety of this application is hereby incorporated by reference for all purposes.

STATEMENT REGARDING FEDERALLY FUNDED RESEARCH

This invention was made with government support under CHE1808509 awarded by the National Science Foundation. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 19203US_ST25.txt. The text file is 2 KB, was created on Jan. 4, 2021, and is being submitted electronically via EFS-Web.

BACKGROUND

Collagen is a ubiquitous material that living organisms use to create structures through the self-assembly of fibrillogenic proteins. It is desirable to design improved materials with biological, chemical, and mechanical properties that mimic collagen as it is typically biocompatible. The triple-helical domain of native collagen comprises a recurrence of a tripeptide repeat sequence Xaa-Yaa-Gly. The amino acids in the Xaa and Yaa positions vary; however, from a statistical standpoint, Proline (Pro) and (4R)-hydroxyproline (Hyp), respectively, most frequently occupy these positions. The assembly of synthetic collagen triple helices has been reported. See, e.g., Rele et al. JACS, 2007, 129, 14780-14787; Merg et al. report 2D crystal engineering of nanosheets assembled from helical peptide building blocks. Angew Chem Int Ed Engl. 2019, 58(38):13507-13512, and U.S. Pat. No. 9,725,499. Parmar et al. report folding and self-assembly using designed multicomponent peptide systems. J. Am. Chem. Soc. 2016, 138, 13, 4362-4367.

The self-assembly of synthetic collagen into two- or three-dimensional structures for fabricating artificial medical devices or implantable material has been challenging. Thus, there is a need to identify improved materials.

References cited herein are not an admission of prior art.

SUMMARY

This disclosure relates to collagen-like polypeptides and materials containing the same and uses in biomedical applications. In certain embodiments, this disclosure contemplates that collagen-like polypeptides and materials containing the same are functionalized with proteins or small molecules to create useful scaffolds for drug delivery or testing. In certain embodiments, collagen-like polypeptides and materials containing the same are used in cardiac patches, cosmetic surgery, bone grafts, tissue regeneration, and wound healing.

In certain embodiments, this disclosure contemplates materials disclosed herein comprising functional groups are displayed at the surface and useful for non-covalent (e.g., biotin) or covalent (e.g., azide group) capture of complementarily functionalized substrates (e.g., streptavidin and dibenzocyclo-octyne labels, respectively) using affinity interactions and copper-free click (i.e., Huisgen cyclization) reaction, respectively. Using these methods, one can provide spatially-selective functionalization with synthetic fluorophores and fluorescent proteins (e.g., green fluorescent protein, GFP) using fluorescence microscopy.

In certain embodiments, collagen-like polypeptides and materials containing the same are in the form of tubes/cylinders, and sheets produced from distinct polypeptides with (positively charged triads)m-(Pro-Hyp-Gly)n and (Pro-Hyp-Gly)n'-(negatively charged triads)p, in which m, n, n', and p are integers. Neither m and p nor n and n' need to be equal to each other. In certain embodiments, a pair of peptide sequences are described by (Pro-Arg-Gly)$_4$-(Pro-Hyp-Gly)$_6$ (R4P6) (SEQ ID NO: 1) and (Pro-Hyp-Gly)$_6$-(Glu-Hyp-Gly)$_4$ (P6E4) (SEQ ID NO: 2), in which m=p=4 and n=n'=6. The individual peptides form stable triple helices. When the peptides are mixed at appropriate pH, the formation of tubes is observed in which the outer (convex) surface is defined by the charged triads and the inner (concave) surface is defined by the Pro-Hyp-Gly triads.

In certain embodiments, this disclosure relates to a material comprising a first polypeptide and a second polypeptide, wherein the first polypeptide comprises a) a first terminal segment comprising a three amino acid repeat starting with two amino acids, wherein one of the two amino acids is a hydrophobic amino acid, one of the two amino acids is an amino acid comprising a side-chain substituted with a basic nitrogen containing group, and ending with a glycine, followed by b) a second terminal segment comprising a three amino acid repeat starting with two amino acids, wherein one of the two amino acids is a hydrophobic amino acid, wherein one of the two amino acids comprises a side chain with an hydroxy group, and ending with a glycine; and wherein the second polypeptide comprises a) a first terminal segment comprising a three amino acid repeat starting with two amino acids, wherein one of the two amino acids is a hydrophobic amino acid, wherein one of the two amino acids comprises a side chain with an hydroxy group, and ending with a glycine, followed by b) a second terminal segment comprising a three amino acid repeat starting with two amino acids, wherein one of the two amino acids is an amino acid comprising a side chain substituted with a carboxylic acid group, wherein one of the two amino acids comprises a side chain with an hydroxy group, and ending with a glycine. In certain embodiments, the material is in the form of a cylinder or a sheet.

In certain embodiments, the first polypeptide comprises more amino acids than the second polypeptide. In certain embodiments the first polypeptide is (Pro-Arg-Gly)6-(Pro-Hyp-Gly)6 (R6P6) (SEQ ID NO: 3). In certain embodiments, the second polypeptide comprises more amino acids than the first polypeptide. In certain embodiments, a ligand, receptor, drug, or fluorescent molecule is conjugated to the first polypeptide. In certain embodiments, a ligand, receptor, drug, or fluorescent molecule is conjugated to the second polypeptide.

In certain embodiments, the first terminal segment of the first polypeptide comprises a three amino acid repeat starting with two amino acids, wherein one of the two amino acids is proline, and one of the two amino acids is an amino acid comprising a side chain substituted with a guanidine group, and ending with a glycine.

In certain embodiments, the second terminal segment of the first polypeptide comprises a three amino acid repeat starting with two amino acids, wherein one of the two amino acids is proline, one of the two amino acids comprises a side chain with an hydroxy group, and ending with a glycine.

In certain embodiments, the first terminal segment of the second polypeptide comprises a three amino acid repeat starting with two amino acids, wherein one of the two amino acids is proline, and one of the two amino acids is hydroxyproline, and ending with a glycine.

In certain embodiments, the second terminal segment of the second polypeptide comprises a three amino acid repeat starting with two amino acids, wherein one of the two amino acids is an amino acid comprising a side-chain substituted with a carboxylic acid group, one of the two amino acids is hydroxy proline, and ending with a glycine.

In certain embodiments, the hydrophobic amino acid is proline. In certain embodiments, the basic nitrogen containing group is selected from an amino, imine, guanidine, imidazole, and pyridine group. In certain embodiments, the amino acid comprising a side chain substituted with a basic nitrogen containing group is selected from arginine, histidine, lysine, amino-phenyl alanine, pyridyl alanine, and aminoproline. In certain embodiments, the amino acid comprising a side chain substituted with a carboxylic acid group is glutamic acid or aspartic acid.

In certain embodiments, the first terminal segment is the N-terminal segment and the second terminal segment is the C-terminal segment. In certain embodiments, the first terminal segment is the N-terminal segment and the N-terminal amino acid is proline In certain embodiments, this disclosure relates to materials comprising a first polypeptide and a second polypeptide, wherein the first polypeptide has the formula $(X^1-Y^1-Gly)m-(X^2-Y^2-Gly)n$, wherein, $X^1$ is any amino acid, $Y^1$ is any amino acid, m is three or more, provided that proline is the most common $X^1$, provided that an amino acid comprising a side-chain substituted with a basic nitrogen containing group is the most common $Y^1$; $X^2$ is any amino acid, $Y^2$ is any amino acid, n is three or more, provided that proline is the most common $X^2$, provided that an amino acid comprising a side chain with a hydroxy group is the most common $Y^2$; and wherein the second polypeptide has the formula $(X^3-Y^3-Gly)p-(X^4-Y^4-Gly)q$, wherein, $X^3$ is any amino acid, $Y^3$ is any amino acid, p is three or more, provided that proline is the most common $X^3$, provided that an amino acid comprising a side-chain substituted with a basic nitrogen containing group is the most common $Y^3$; $X^4$ is any amino acid, $Y^4$ is any amino acid, q is three or more, provided that amino acid comprising a side-chain substituted with a carboxylic acid group is the most common $X^4$, provided that an amino acid comprising a side chain with a hydroxy group is the most common $Y^4$.

In certain embodiments, this disclosure relates to materials comprising a first polypeptide, a second polypeptide, and a third polypeptide, wherein the first polypeptide has the formula $(X^1-Y^1-Gly)m-(X^2-Y^2-Gly)n$, wherein, $X^1$ is any amino acid, $Y^1$ is any amino acid, m is three or more, provided that proline is the most common $X^1$, provided that an amino acid comprising a side-chain substituted with a basic nitrogen containing group is the most common $Y^1$; $X^2$ is any amino acid, $Y^2$ is any amino acid, n is three or more, provided that proline is the most common $X^2$, provided that an amino acid comprising a side chain with a hydroxy group is the most common $Y^2$; wherein the second polypeptide has the formula $(X^3-Y^3-Gly)_p-(X^4-Y^4-Gly)_q$, wherein, $X^3$ is any amino acid, $Y^3$ is any amino acid, p is three or more, provided that proline is the most common $X^3$, provided that an amino acid comprising a side-chain substituted with a basic nitrogen containing group is the most common $Y^3$; $X^4$ is any amino acid, $Y^4$ is any amino acid, q is three or more, provided that amino acid comprising a side-chain substituted with a carboxylic acid group is the most common $X^4$, provided that an amino acid comprising a side chain with a hydroxy group is the most common $Y^4$; and wherein the third polypeptide has the formula $(X^5-Y^6-Gly)_r-(X^2-Y^2-Gly)_t$, wherein, $X^5$ is any amino acid, $Y^6$ is any amino acid, r is an integer greater than m, provided that proline is the most common $X^5$, provided that an amino acid comprising a side-chain substituted with a basic nitrogen containing group is the most common $Y^6$; $X^2$ is any amino acid, $Y^2$ is any amino acid, t is an integer equal to n, provided that proline is the most common $X^2$, provided that an amino acid comprising a side chain with a hydroxy group is the most common $Y^2$.

In certain embodiments, $X^5$ is $X^1$ and $Y_6$ is $Y^1$. In certain embodiments, $X^5$ is $X^1$. In certain embodiments, $Y_6$ is $Y^1$. In certain embodiments, the material is in the form of a cylinder or sheet. In certain embodiments, $X^1$ is proline and $Y^1$ is selected from arginine, histidine, lysine, amino-phenyl alanine, pyridyl alanine, and aminoproline. In certain embodiments, the $X^2$ is proline and $Y^2$ is hydroxyproline. In certain embodiments, the $X^3$ is proline and $Y^3$ is hydroxyproline. In certain embodiments, the $X^4$ is glutamic acid or aspartic acid and $Y^4$ is hydroxyproline.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

Figure 1A:
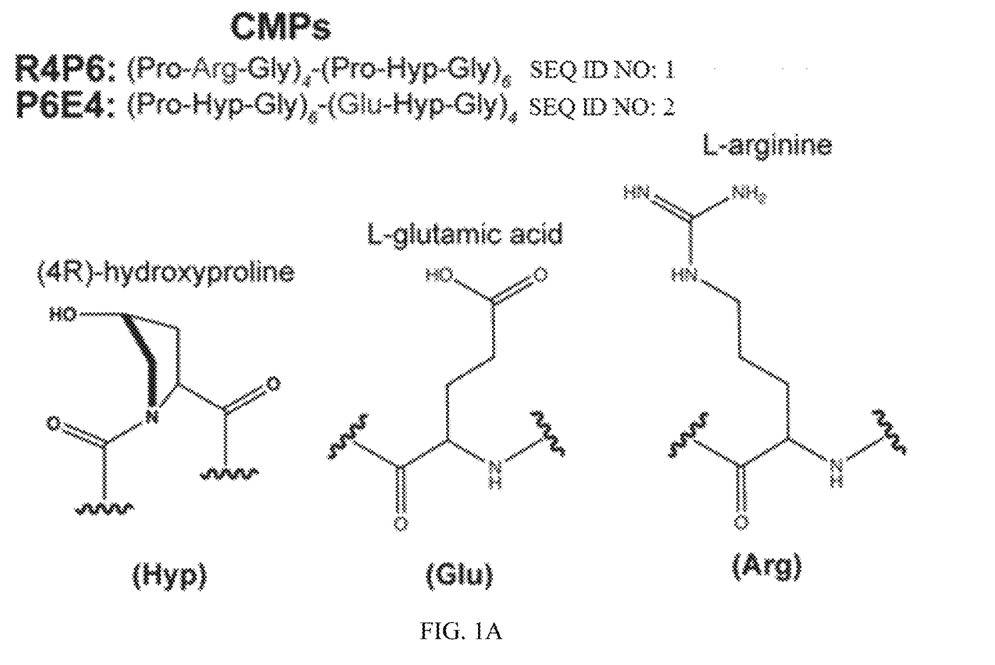
FIG. 1A shows the amino acid sequences of developed CMPs: R4P6 (SEQ ID NO: 1) and P6E4 (SEQ ID NO: 2).
Figure 1B:
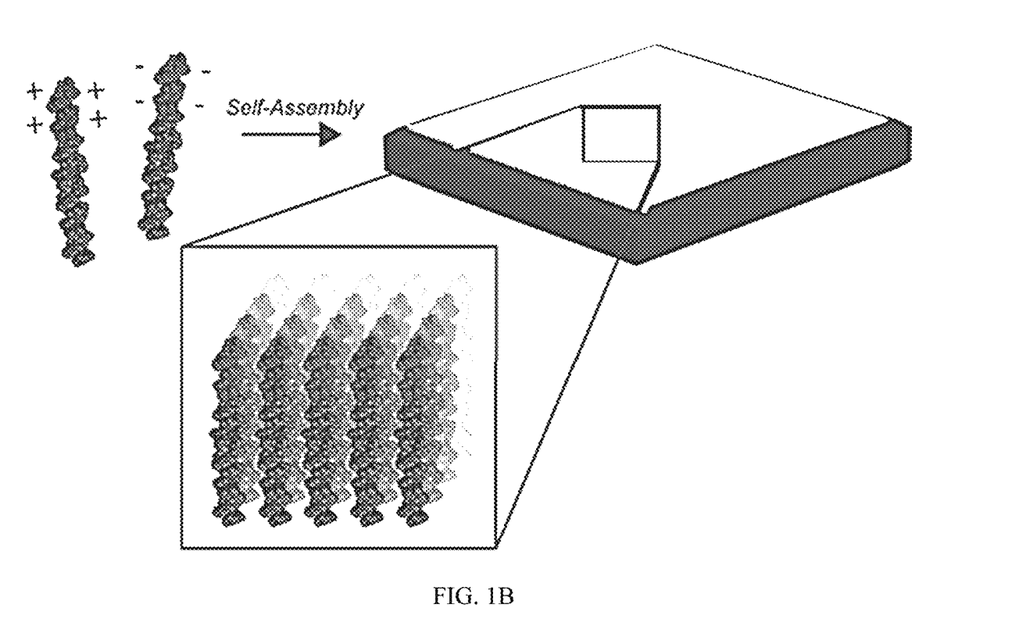
FIG. 1B illustrates assembly schematic for multicomponent 2D peptide nanosheets comprised of peptides R4P6 and P6E4.

Multicomponent Collagen Based Mimetic Peptide (CMP) System Designed to Pack Antiparallel A multicomponent CMP system was designed to pack antiparallel to provide favorable coulombic interactions between helices therefore promoting the formation of well-defined and structurally homogeneous structures. Moreover, the asymmetric peptide sequences assemble into mesoscale collagen tubes, collagen nanosheets and exhibit pH responsiveness transitioning between morphologies. The preparation of a family of CMPs of varying length and amino acid content were designed to assemble into well-defined structures. Through manipulation of peptide sequence and experimental conditions, one can mediate a transition between assembly morphology, which has not previously been demonstrated for a multicomponent peptide system comprised of these collagen-based materials. The general formula for reported CMPs and initial peptide sequences are termed R4P6 and P6E4 (FIG. 1A).

The materials utilize the structural motif of the collagen triple helix, acting as a rigid rod, to expand the assembly space in the literature "soft" materials through a bottom-up assembly process. Additionally, the reported structures possess unique properties in size. Lastly, this construct is a pH responsive system. These materials are contemplated for possible incorporation into artificial biological tissues, delivery vehicles, sensory devices, and reaction vessels.

Assemblies or Collagen Based Mimetic Peptide

In certain embodiments, this disclosure contemplates that collagen-like polypeptides and materials containing the same functionalized with proteins or small molecules to create useful scaffolds for drug delivery or testing.

In certain embodiments, this disclosure contemplates materials disclosed herein comprising functional groups are displayed at the surface and may be used for non-covalent (e.g., biotin) or covalent (e.g., azide group) capture of complementarily functionalized substrates (e.g., streptavidin and dibenzocyclo-octyne labels, respectively) using affinity interactions and copper-free click (i.e., Huisgen cyclization) reaction, respectively. Using these methods, one can provide spatially-selective functionalization with synthetic fluorophores and fluorescent proteins (e.g., green fluorescent protein, GFP) using fluorescence microscopy.

In certain embodiments, collagen-like polypeptides and materials containing the same are in the form of tubes/cylinders, and sheets produced from distinct polypeptides with (positively charged triads)m-(Pro-Hyp-Gly)n and (Pro-Hyp-Gly)n'-(negatively charged triads)p, in which m, n, n', and p are integers. Neither m and p nor n and n' need to be equal to each other. In certain embodiments, a pair of peptide sequences are described by $(Pro-Arg-Gly)_4$-$(Pro-Hyp-Gly)_6$ (R4P6) (SEQ ID NO: 1) and $(Pro-Hyp-Gly)_6$-$(Glu-Hyp-Gly)_4$ (P6E4) (SEQ ID NO: 2), in which m=p=4 and n=n'=6. In certain embodiments, a pair of peptide sequences are described by $(Pro-Arg-Gly)_6$-$(Pro-Hyp-Gly)_6$ (R6P6) (SEQ ID NO: 3) and $(Pro-Hyp-Gly)_6$-$(Glu-Hyp-Gly)_4$ (P6E4) (SEQ ID NO: 2), in which m=6, p=4 and n=n'=6. The individual peptides form stable triple helices. However, when the peptides are mixed at appropriate pH, the formation of tubes is observed in which the outer (convex) surface is defined by the charged triads and the inner (concave) surface is defined by the Pro-Hyp-Gly triads.

In certain embodiments, this disclosure relates to a material comprising a first polypeptide and a second polypeptide, wherein the first polypeptide comprises a) a first terminal segment comprising a three amino acid repeat starting with two amino acids, wherein one of the two amino acids is a hydrophobic amino acid, one of the two amino acids is an amino acid comprising a side-chain substituted with a basic nitrogen containing group, and ending with a glycine, followed by b) a second terminal segment comprising a three amino acid repeat starting with two amino acids, wherein one of the two amino acids is a hydrophobic amino acid, wherein one of the two amino acids comprises a side chain with an hydroxy group, and ending with a glycine; and wherein the second polypeptide comprises a) a first terminal segment comprising a three amino acid repeat starting with two amino acids, wherein one of the two amino acids is a hydrophobic amino acid, wherein one of the two amino acids comprises a side chain with an hydroxy group, and ending with a glycine, followed by b) a second terminal segment comprising a three amino acid repeat starting with two amino acids, wherein one of the two amino acids is an amino acid comprising a side chain substituted with a carboxylic acid group, wherein one of the two amino acids comprises a side chain with an hydroxy group, and ending with a glycine. In certain embodiments, the material is in the form of a cylinder or a sheet.

In certain embodiments, the first polypeptide comprises more amino acids than the second polypeptide. In certain embodiments, the second polypeptide comprises more amino acids than the first polypeptide. In certain embodiments, a ligand, receptor, or fluorescent molecule is conjugated to the first polypeptide. In certain embodiments, a ligand, receptor, or fluorescent molecule is conjugated to the second polypeptide.

In certain embodiments, the first terminal segment of the first polypeptide comprises a three amino acid repeat starting with two amino acids, wherein one of the two amino acids is proline, and one of the two amino acids is an amino acid comprising a side chain substituted with a guanidine group, and ending with a glycine.

In certain embodiments, the second terminal segment of the first polypeptide comprises a three amino acid repeat starting with two amino acids, wherein one of the two amino acids is proline, one of the two amino acids comprises a side chain with an hydroxy group, and ending with a glycine.

In certain embodiments, the first terminal segment of the second polypeptide comprises a three amino acid repeat starting with two amino acids, wherein one of the two amino acids is proline, and one of the two amino acids is hydroxyproline, and ending with a glycine.

In certain embodiments, the second terminal segment of the second polypeptide comprises a three amino acid repeat starting with two amino acids, wherein one of the two amino acids is an amino acid comprising a side-chain substituted with a carboxylic acid group, one of the two amino acids is hydroxy proline, and ending with a glycine.

In certain embodiments, the hydrophobic amino acid is proline. In certain embodiments, the basic nitrogen containing group is selected from an amino, imine, guanidine, imidazole, and pyridine group. In certain embodiments, the amino acid comprising a side chain substituted with a basic nitrogen containing group is selected from arginine, histidine, lysine, amino-phenyl alanine, pyridyl alanine, and aminoproline. In certain embodiments, the amino acid comprising a side chain substituted with a carboxylic acid group is glutamic acid or aspartic acid.

In certain embodiments, the first terminal segment is the N-terminal segment and the second terminal segment is the C-terminal segment. In certain embodiments, the first terminal segment is the N-terminal segment and the N-terminal amino acid is proline In certain embodiments, this disclosure relates to materials comprising a first polypeptide and a second polypeptide, wherein the first polypeptide has the formula $(X^1-Y^1-Gly)m-(X^2-Y^2-Gly)n$, wherein, $X^1$ is any amino acid, $Y^1$ is any amino acid, m is three or more, provided that proline is the most common $X^1$, provided that an amino acid comprising a side-chain substituted with a basic nitrogen containing group is the most common $Y^1$; $X^2$ is any amino acid, $Y^2$ is any amino acid, n is three or more, provided that proline is the most common $X^2$, provided that an amino acid comprising a side chain with a hydroxy group is the most common $Y^2$; and wherein the second polypeptide has the formula $(X^3-Y^3-Gly)p-(X^4-Y^4-Gly)q$, wherein, $X^3$ is any amino acid, $Y^3$ is any amino acid, p is three or more, provided that proline is the most common $X^3$, provided that an amino acid comprising a side-chain substituted with a basic nitrogen containing group is the most common $Y^3$; $X^4$ is any amino acid, $Y^4$ is any amino acid, q is three or more, provided that amino acid comprising a side-chain substituted with a carboxylic acid group is the most common $X^4$, provided that an amino acid comprising a side chain with a hydroxy group is the most common $Y^4$.

In certain embodiments, $X^1$ is proline and $Y^1$ is selected from arginine, histidine, lysine, amino-phenyl alanine, pyridyl alanine, and aminoproline. In certain embodiments, the $X^2$ is proline and $Y^2$ is hydroxyproline. In certain embodiments, the $X^3$ is proline and $Y^3$ is hydroxyproline. In certain embodiments, the $X^4$ is glutamic acid or aspartic acid and $Y^4$ is hydroxyproline.

In certain embodiments, this disclosure relates to materials comprising a first polypeptide, a second polypeptide, and a third polypeptide, wherein the first polypeptide has the formula $(X^1-Y^1-Gly)_m-(X^2-Y^2-Gly)_n$, wherein, $X^1$ is any amino acid, $Y^1$ is any amino acid, m is three or more, provided that proline is the most common $X^1$, provided that an amino acid comprising a side-chain substituted with a basic nitrogen containing group is the most common $Y^1$; $X^2$ is any amino acid, $Y^2$ is any amino acid, n is three or more, provided that proline is the most common $X^2$, provided that an amino acid comprising a side chain with a hydroxy group is the most common $Y^2$; wherein the second polypeptide has the formula $(X^3-Y^3-Gly)_p-(X^4-Y^4-Gly)_q$, wherein, $X^3$ is any amino acid, $Y^3$ is any amino acid, p is three or more, provided that proline is the most common $X^3$, provided that an amino acid comprising a side-chain substituted with a basic nitrogen containing group is the most common $Y^3$; $X^4$ is any amino acid, $Y^4$ is any amino acid, q is three or more, provided that amino acid comprising a side-chain substituted with a carboxylic acid group is the most common $X^4$, provided that an amino acid comprising a side chain with a hydroxy group is the most common $Y^4$; and wherein the third polypeptide has the formula $(X^5-Y^6-Gly)_r-(X^2-Y^2-Gly)_t$, wherein, $X^5$ is any amino acid, $Y^6$ is any amino acid, r is an integer greater than m, provided that proline is the most common $X^5$, provided that an amino acid comprising a side-chain substituted with a basic nitrogen containing group is the most common $Y^6$; $X^2$ is any amino acid, $Y^2$ is any amino acid, t is an integer equal to n, provided that proline is the most common $X^2$, provided that an amino acid comprising a side chain with a hydroxy group is the most common $Y^2$.

In certain embodiments, $X^5$ is $X^1$ and $Y_6$ is $Y^1$. In certain embodiments, $X^5$ is $X^1$. In certain embodiments, $Y_6$ is $Y^1$. In certain embodiments, the material is in the form of a cylinder or sheet. In certain embodiments, $X^1$ is proline and $Y^1$ is selected from arginine, histidine, lysine, amino-phenyl alanine, pyridyl alanine, and aminoproline. In certain embodiments, the $X^2$ is proline and $Y^2$ is hydroxyproline. In certain embodiments, the $X^3$ is proline and $Y^3$ is hydroxyproline. In certain embodiments, the $X^4$ is glutamic acid or aspartic acid and $Y^4$ is hydroxyproline.

In certain embodiments, m is 2 to 1000, or 3 to 100, or 4 to 20, or 4 to 10, n is 2 to 1000, or 3 to 100, or 4 to 20, or 4 to 10, p is 2 to 1000, or 3 to 100, or 4 to 20, or 4 to 10, q is 2 to 1000, or 3 to 100, or 4 to 20, or 4 to 10.

In certain embodiments, n or q is greater than m and p, or n or q is less than m and p, or n or q is different than m and p, or n, m, p and q are the same, or n is m plus 1-4 or m minus 1-4, or n is p plus 1-4 or p minus 1-4, or m is n plus 1-4 or n minus 1-4, or m is p plus 1-4 or p minus 1-4, or p is n plus 1-4 or n minus 1-4, or p is m plus 1-4 or m minus 1-4, or combinations thereof.

In certain embodiments, the disclosure relates a purified polypeptide of SEQ ID NO: 1, 2, 3 or functioning variants thereof e.g., with one or two amino acid substitutions, additions, deletions; or variants thereof with three or more amino acid substitutions, additions, deletions.

In certain embodiments, the first terminal segment comprises a three amino acid repeat starting with two amino acids, wherein one of the two amino acids is a hydrophobic amino acid, wherein one of the two amino acids is proline substituted with an amino group, and ending with a glycine.

In certain embodiments, the first terminal segment is the N-terminal segment and the second terminal segment is the C-terminal segment. In certain embodiments, the first terminal segment is the N-terminal segment and the N-terminal amino acid is an amino acid comprising a side-chain substituted with a basic nitrogen containing group. In certain embodiments, the most common N-terminal amino acid is amino proline or proline substituted with an amino group such as (2S,4S)-4-aminoproline.

In certain embodiments, the polypeptide is terminally linked to a polyethylene glycol, biotin, hydrocarbon chain, steroid, therapeutic agent, antibody, antibody epitope, protein, ligand, receptor, oligonucleotide, chelating agent, or combinations thereof.

In certain embodiments, the disclosure relates to two-dimensional material comprising a polypeptide disclosed herein. In certain embodiments the two-dimensional material is a sheet between 8 and 12 nanometers or 8 and 20, or 8 and 30, or 8 and 40, or 8 and 50 nm or more wide or thick.

In certain embodiments, the disclosure relates to two-dimensional material comprising a polypeptide disclosed herein. In certain embodiments the two-dimensional material is a tube/cylinder with an outer diameter between 150 and 250 nanometers. In certain embodiments the two-dimensional material is a tube/cylinder with an outer diameter between 200 and 400 nanometers and an inner diameter between 50 and 150 nanometers. In certain embodiments the two-dimensional material is a tube/cylinder with an outer diameter between 150 and 250 nanometers and an inner diameter between 50 and 150 nanometers.

In certain embodiments, the two-dimensional material disclosed herein has two or more polypeptides that are not identical. In certain embodiments, at least one polypeptide is terminally linked to a polyethylene glycol, biotin, hydrocarbon chain, steroid, therapeutic agent, antibody, antibody epitope, protein, ligand, receptor, oligonucleotide, chelating agent, or combinations thereof.

In certain embodiments, the disclosure relates to three-dimensional materials comprising a material disclosed herein. In certain embodiments, the three-dimensional material is glass, ceramic, silicon wafer, fluoropolymer, metal, metal oxide, semi-conducting material, transparent polymer, opaque polymer, medical device, implantable device or combinations thereof.

In certain embodiments, the disclosure relates to methods of making a two- or three-dimensional material comprising mixing a polypeptide disclosed herein in a liquid under conditions such that a solid comprising the polypeptide forms. In certain embodiments the solid is in the form of a sheet or tube/cylinder.

EXAMPLES

Synthesis and Purification.

A CEM Liberty microwave-assisted peptide synthesizer was employed to make the following peptides: R4P6, Biotin-R6P6, P6E4, and CP262. Standard Fmoc protection chemistry was used with Fmoc-Gly-HMP-TentaGel™ resin. HBTU and DIEA were employed as the activator and activator base, respectively, with deprotection of Fmoc groups through the use of 20% piperidine in DMF. Crude peptide products were subjected to cleavage from the support resin through standard protocol consisting of 92.5% TFA, 2.5% TIS, 2.5% DODT, and 2.5% water (TFA: trifluoroacetic acid, DODT: 3,6-Dioxa-1,8-octanedithiol, TIS: Triisopropylsilane). Peptides were precipitated from solution through centrifugation at 4° C. after mixing with cold Et2O. A Shimadzu LC-20AP preparatory scale reverse-phase HPLC with a C18 column was used to purify and re-purify peptides. A linear gradient of water-acetonitrile was used with 0.1% TFA. After collection of desired products, samples were assessed using matrix-assisted laser desorption/ionization time of flight (MALDI-TOF) mass spectrometry with CHCA matrix (CHCA: α-Cyano-4-hydroxycinnamic acid). Peptides were dialyzed against pure HPLC grade water to remove remaining TFA in 2,000 Da dialysis containers, lyophilized, and stored at −20° C. Known amounts of peptide were weighed using an analytical balance and dissolved in water before being separated into known amounts, lyophilized and stored at −20° C. prior to assembly.

For assembly, peptides were dissolved using IVIES, MOPS, and TAPS (20 mM pH 6, pH 7, and pH 8, respectively) at appropriate concentrations. All samples were annealed from 90° C. to 4° C. or 90° C. to 25° C. at a gradient of 0.2° C./min and stored at 4° C. or room temperature. Arginine containing peptides were annealed first using an annealing protocol from 90° C. to 4° C. and allowed to sit for at least one week. Next, glutamic acid peptide, P6E4, was annealed 90° C. to 25° C. and added to an arginine containing peptide that had recently been warmed to room temperature. The peptide mixtures were then allowed to incubate at room temperature before characterization.

Both R4P6 and P6E4 contain asymmetric charge distributions across the length of the peptides. Positively charged triads incorporated the natural amino acid, Arginine (Arg), in the Yaa position creating (Pro-Arg-Gly) triads at the N-terminus of R4P6 while negatively charged triads at the C-terminus of P6E4 utilized Glutamic Acid (Glu) in the Xaa position resulting in (Glu-Hyp-Gly) triads. Both peptides contained six canonical pro-triple helix (Pro-Hyp-Gly) triads. Positive and negative residue identity and position were chosen based on prior host-guest studies of collagen-based peptide systems. The respective residues and positions were the most stable collagen substitutions.

Circular Dichroism (CD) Spectropolarimetry Studies

R4P6 and E4P6 for form a triple helical conformation in aqueous buffered solution. A characteristic CD spectrum of the collagen triple helix consists of a maximum peak at 224 nm and a minimum peak at 198 nm. The ratio of the positive peak to the negative peak, termed the RPN value, serves as an indicator of a given peptides propensity for forming a triple helix conformation. An RPN value of ≥0.10 is consistent with a stable triple helix.

Figure 2A:
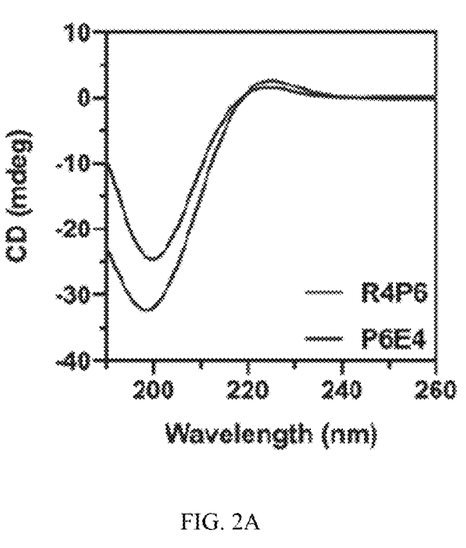
FIG. 2A shows the CD spectra of peptides R4P6 and P6E4 (1 mg/mL) in 20 mM MOPS buffer, pH 7.
Figure 2B:
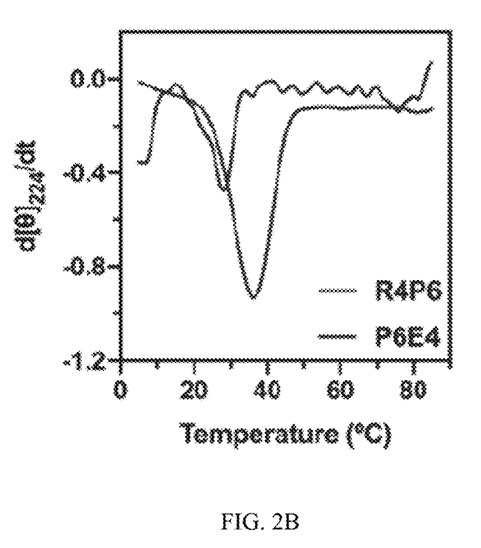
FIG. 2B shows the first derivative plot of the CD signal at 224 nm as a function of increasing temperature for R4P6 and P6E4 (0.5 mg/mL).
Figure 2C:
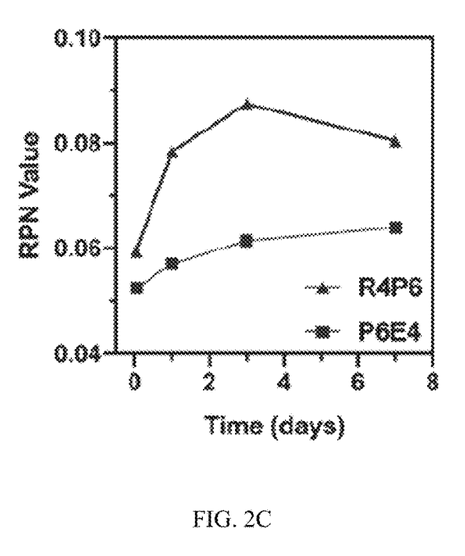
FIG. 2C shows RPN values at the time points of 1 hour, 24 hours, 3 days and 7 days.

R4P6 and P6E4 displayed propensity for forming relatively stable triple helices with RPN values of 0.08 and 0.06, respectively, after incubation for one week at 4° C. RPN values of less than 0.10 can be rationalized on the basis that charged residues at the termini generate unfavorable repulsive forces. In addition to assessing relative helix stability, time studies monitoring the RPN values were utilized to assess the rate of triple helix formation over 1 week (FIG. 2C). P6E4 exhibited a slower rate of formation as observed by the slower increase in RPN value compared to R4P6. The lower RPN values of P6E4 are also indicative of decreased triple helix stability. From these studies, P6E4 was chosen as the rate limiting peptide for all assembly experiments.

Thermal Denaturation Studies

The melting temperature (Tm) was calculated by taking the minimum of the first derivative of the melting curve. In addition to displaying a higher rate of triple helical formation, R4P6 displayed a higher Tm at 37° C. indicating a higher relative stability when compared with P6E4 (Tm=28° C.). It is believed that arginine forms favorable interhelical and intrahelical hydrogen bonds when replacing Hyp in the canonical collagen sequence therefore having significantly less of a destabilizing effect on the formation of the triple helix when compared to other amino acid residues. Comparatively, although Glu placed in the Xaa position is the most stable conformation for negatively charged residues, it results in a significant decrease in helix stability as exhibited by the RPN value and Tm.

R4P6 and P6E4 Sheets and Tubes

Figure 3A:
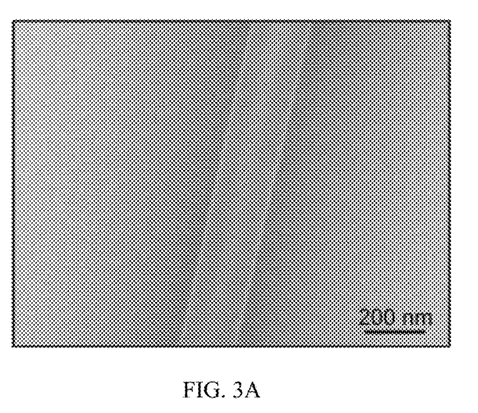
FIG. 3A shows a TEM image at 200 nm of a single representative collagen tube constructed from R4P6 and P6E4.
Figure 3B:
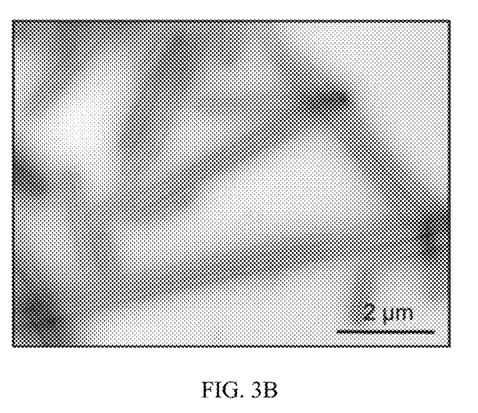
FIG. 3B shows a TEM image at 2 micrometers of a polydisperse group of collagen structures.

After assembly as described above, TEM was employed to interrogate assembled structures after incubation at room temperature for at least one week. In opposition to our original hypothesis that the peptides would form peptide sheets, tubular structures were observed instead. No evidence of ordered assembly was observed upon imaging single peptide solutions, which suggests that assembly of the peptides is dependent the presence of both in solution. The collagen tubes displayed highly polydisperse characteristics including variation in length along the long axis as well as diameter and wall thickness. FIGS. 3A and 3B displays representative tubes of varying structural dimensions.

Figure 4A:
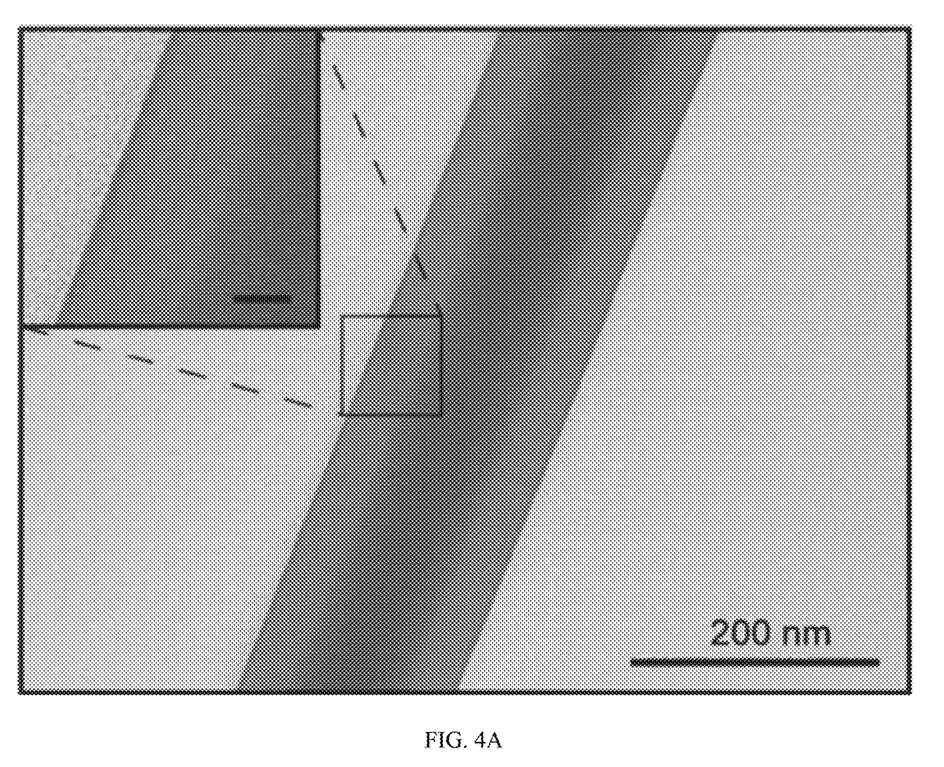
FIG. 4A shows an image of a R4P6/P6E4 tube for visualization of distinct layering. Inset scale bar is equal to 20 nm.
Figure 4B:
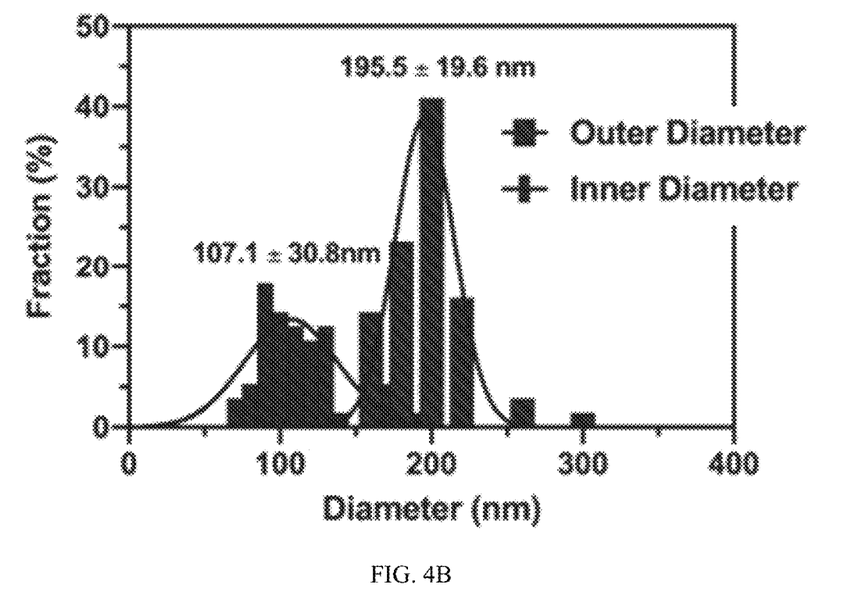
FIG. 4B shows histogram of outer diameter and inner diameter for R4P6/P6E4 tubes. A Gaussian distribution was fitted to each of the histograms with the average and standard deviation displayed above plot (N=56).
Figure 4C:
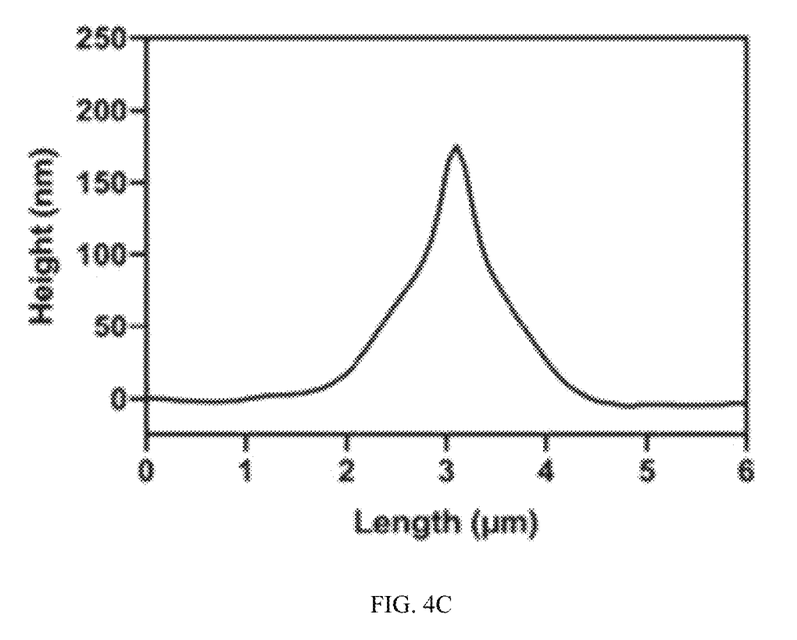
FIG. 4C shows line trace data depicting the height of a tube from AFM tapping mode topography image of R4P6/P6E4 peptide tubes.
Figure 5:
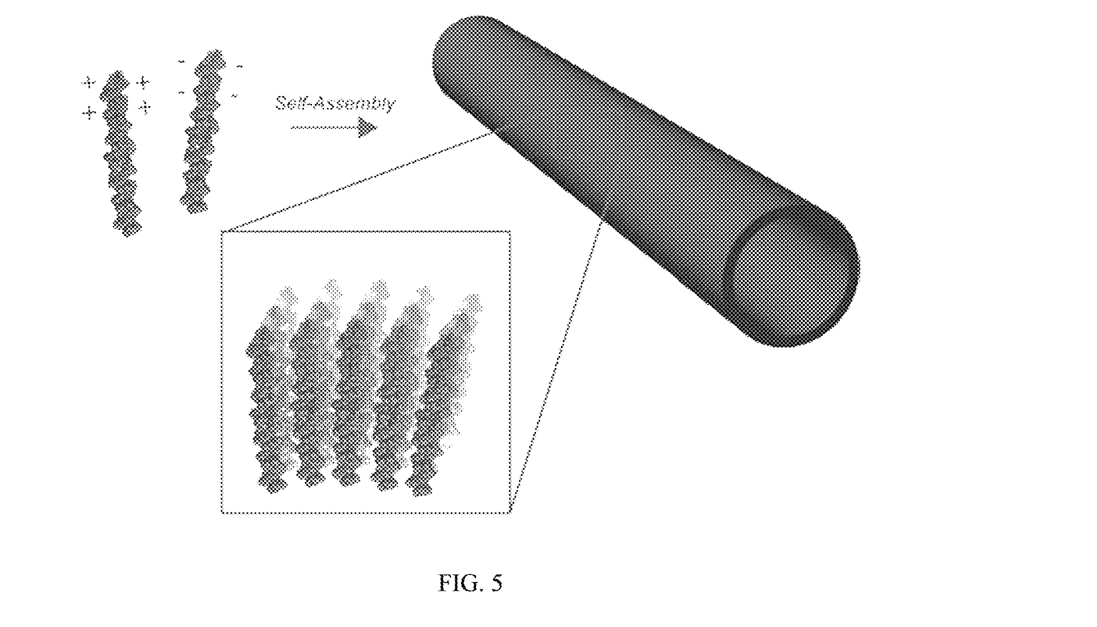
FIG. 5 illustrates an assembly schematic for the formation of multicomponent tubes.

Assembly size distributions were made through assessing the dimensions of many (N=56) structures, which were found to be 107.1±30.8 nm in inner diameter and 195.5±19.6 nm in outer diameter. The difference between the diameters represents the tube wall thickness. At higher magnifications, it becomes possible to visualize distinct layers within the tube walls. The thickness of a single lamellar structure is 11.4±1.1 nm. This value roughly corresponds with the expected height for a sheet comprised of peptides 30 residues in length based off the proposed assembly model for a multicomponent peptide sheet (FIGS. 4A and 4B). The theoretical height of a collagen triple helix, which represents the height of a sheet where helices pack laterally, is calculated to be 0.286 nm per residue, or 8.58 nm for a 30-residue peptide. Atomic force microscopy (AFM) was employed to assess the height of assembled structures. AFM analysis determined that the average height for R4P6/P6E4 structures was 159±17 nm (N=3). AFM measurements are consistent with the formation of tubes on the scale of over 100 nm in diameter. These results in conjunction with results from TEM are complementary in providing evidence for the structural morphology of the assemblies.

Although it is not intended that embodiments of this disclosure are limited by any particular mechanism, it is believed that placing charged residues at only a single terminus (i.e. asymmetric distribution of charged groups) resulted in a distortion to the assembly as a nanosheet where adjacent helices no longer packed parallel to one another resulting in a sheet that curves into a tubular form with many layers.

R6P6 and P6E4 Sheets and Tubes

Figure 6:
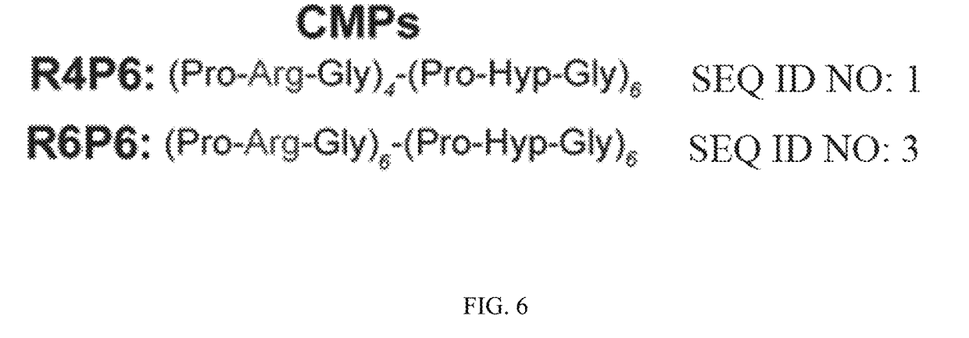
FIG. 6 illustrates the peptide sequence for R6P6 (CP262) (SEQ ID NO: 3) as compared to R4P6 (SEQ ID NO: 1), and the proposed assembly schematic for CP 262 as a peptide nanosheets.

In pursuit of producing a structurally homogeneous population of collagen tubes with identical diameter and wall thickness, a modification to the sequence of R4P6 was introduced to include two additional positively charged triads at the N-terminus, terming the new sequence, R6P6 (i.e. increased m=4 to m=6 based on FIG. 1A, SEQ ID NO: 3 in FIG. 6). The new peptide sequence, R6P6, was designed to have extra positively charged triads protruding from the surface of the peptide tubes with the intention of serving two purposes: firstly, the extra charged triads would prevent the addition of layers to the structures, and secondly, the additional charged triads would create a positive surface charge on the structures thereby preventing non-specific aggregation.

R6P6 was examined through CD spectropolarimetry at various pH conditions (pH 6, 7, and 8). R6P6 demonstrated similar stability to R4P6 with the formation of a stable triple helix at an RPN value of 0.08. R6P6 displayed a slightly higher Tm (pH 7) at 46° C., which is attributable to the two additional charged triads at the N-terminus.

Figure 7A:
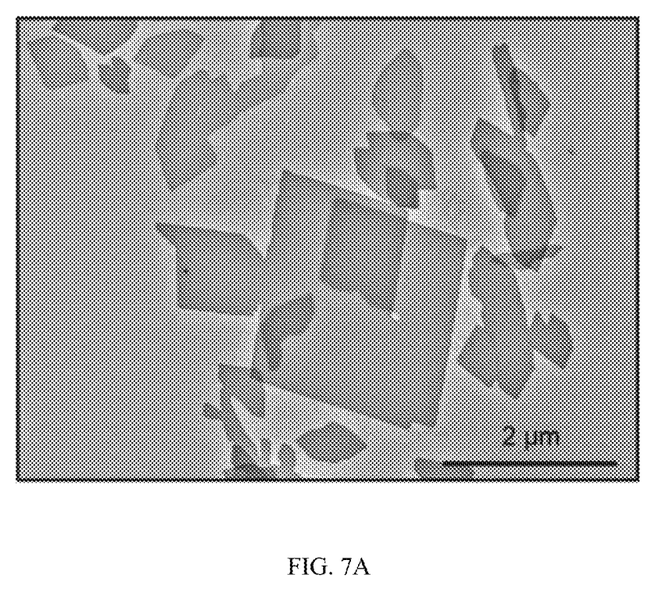
FIG. 7A shows large R6P6/P6E4 peptide sheets formed at pH 7 (similar to pH 6 structures).
Figure 7B:
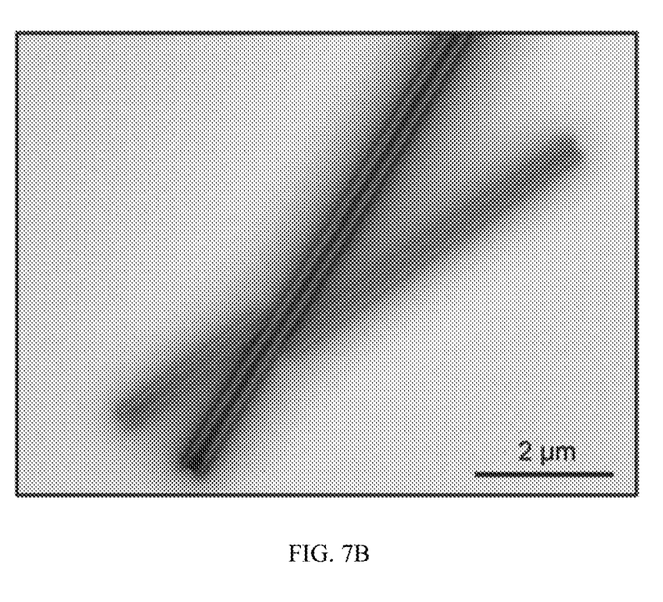
FIG. 7B shows a low magnification image of pH 8 R6P6/P6E4 peptide tubes.
Figure 7C:
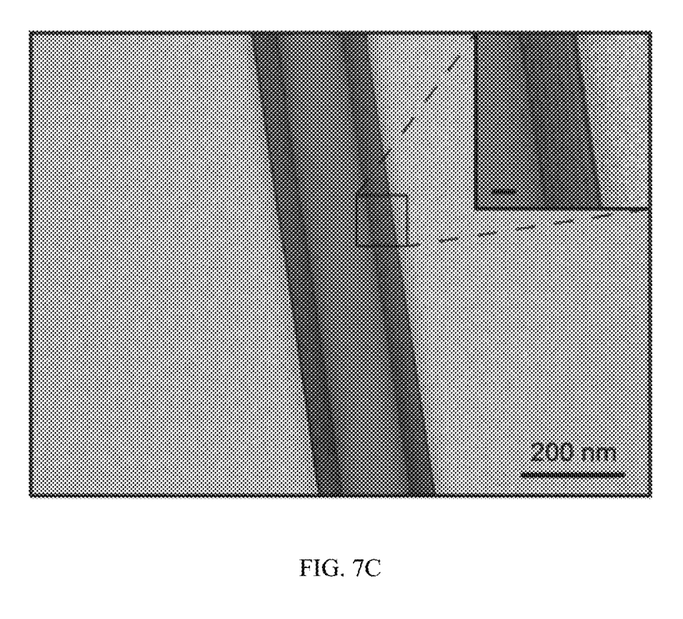
FIG. 7C shows higher magnification image of a R4P6/P6E4 tube for visualization of distinct layering. Inset scale bar is equal to 20 nm.
Figure 7D:
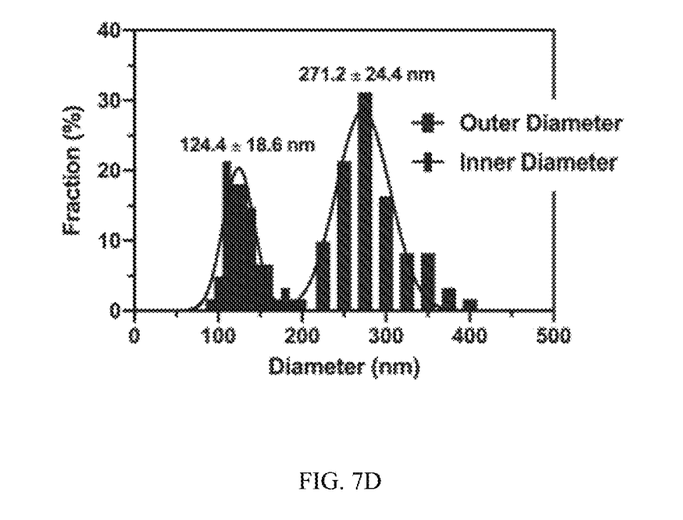
FIG. 7D shows a histogram of outer diameter and inner diameter for R6P6/P6E4 tubes. A Gaussian distribution was fitted to each of the histograms with the average and standard deviation displayed above plot (N=61).

Assembly experiments utilizing P6E4 as the complementary negatively charged peptide were conducted over a range of pH conditions. Results indicate that at pH 6 and 7, R6P6 assembled with P6E4 into large polydisperse irregularly shaped nanosheets (FIG. 7A). While at pH 8, R6P6 was observed to assemble into well-defined tubes larger than those formed using R4P6. R6P6 was observed to form large collagen tubes at pH 8 (FIG. 7B) similar to those observed initially with R4P6. The structures exhibited little or no propensity towards nonspecific aggregation, but the additional charged blocks did not prevent the addition of layers to the tube structure. On the contrary, the R6P6 tubes were observed to contain a higher level of layering with an average of ~6 layers compared to an average of ~3 layers for the R4P6 derived tubes (FIG. 7C). The inner diameter of the R6P6/P6E4 peptide tubes was found to be 124.4±18.6 nm with an outer diameter of 271.2±24.4 nm (FIG. 7D). The average width of each layer was 11.9±4.6 nm, which is similar to the theoretical height of 10.3 nm for a CMP containing 36 residues.

Consistent with prior AFM height measurements of collagen-based materials, the height of R6P6 a pH 7 peptide sheet was 11.3±1.4 nm averaged across the width of the sheet. This value is slightly greater than the theoretical height for the taller of the two peptides, R6P6, but is reasonably consistent with the formation of single layer peptide sheets.

Mixed Assemblies

Figure 8A:
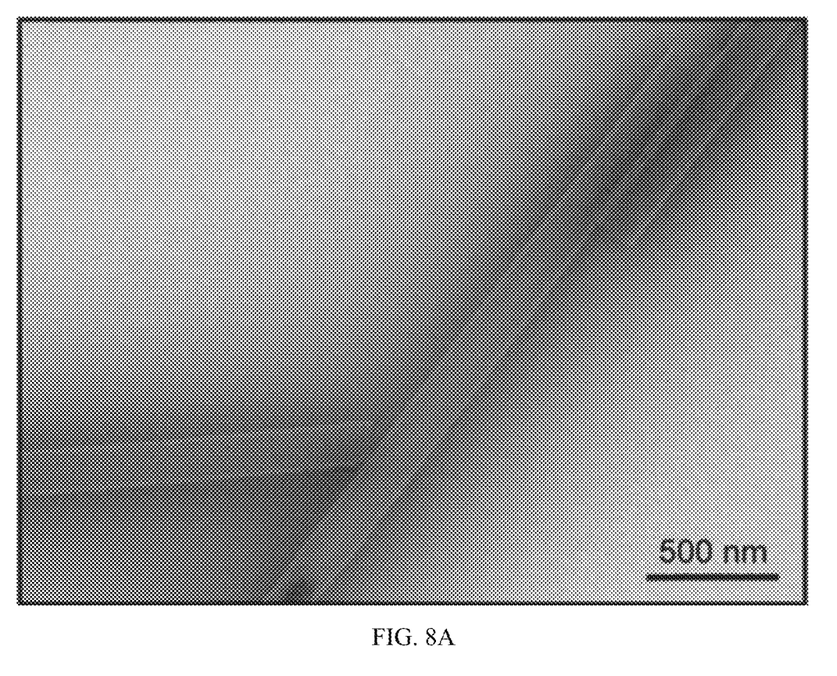
FIG. 8A shows a TEM image of doped (50% R4P6/50% R6P6)/P6E4 single walled tubes.
Figure 8B:
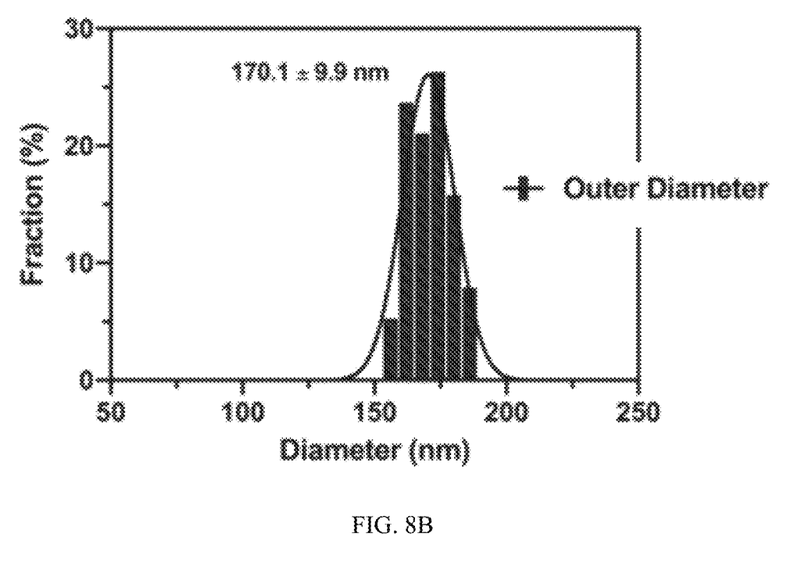
FIG. 8B shows a histogram of the outer diameter of doped (50% R4P6/50% R6P6)/P6E4 single walled tubes. A Gaussian distribution was fitted to the histogram with the average and standard deviation displayed above plot.

While continuing to work towards developing a structurally homogeneous population of single layer peptide tubes, R4P6 and R6P6 were mixed into the assemblies with each other. These so-called "doping" experiments incorporated a series of ratios of the two peptides. The doped experiments ranged from forming entirely sheets with more R6P6 to entirely tubes with more R4P6. Furthermore, the ratios 50%/50% and 75%/25% of R4P6/R6P6 assembled into only single layer tubes with some interspersed sheets. Analysis of the tri-peptide single layer collagen tubes from TEM indicates the creation of a more monodisperse population of structures than was found using either peptide on its own. The doped in R6P6 incorporates itself randomly into the structure resulting in the tubes inability to form stable layered packing (FIGS. 8A and 8B).

Introduction of the R6P6 peptide to the system allowed for two significant developments: first, R6P6 self-assembles into structures that are more well-defined than those assembled from R4P6, and second, the incorporation of R6P6 allows for a pH mediated transition between sheet and tube assemblies. Based on these preliminary experiments, it is believed that the extra charged triads contribute to creating positive surface charge, which, in turn, results in preventing aggregation in situ. In order to study the surface charge of the assemblies, zeta potential measurements for peptide solutions including multilamellar tubes, single walled tubes, and sheets were conducted. If the proposed assembly model was supported, one would expect the zeta potential, as a representation of the surface charge, to increase becoming more positive as the relative amount of R6P6 peptide increased in the assemblies. Experimental data indicates that the R6P6 peptide sheets at pH 6 had the most positive zeta potential ca. +18 mV while the R4P6 peptide tubes at pH 7 displayed the most negative zeta potential of ca. −3 mV. Furthermore, for mixtures of R4P6/R6P6, a gradient of decreasing zeta potential was observed as the ratio of R6P6/R4P6 decreased. The zeta potential measurements support the proposed model where extra positive triads create positive surface charge for the assemblies in solution. However, this does not explain the continued observation of multilamellar tubes as seen with R6P6 assemblies at pH 8. The observation of tubes at pH 8 compared to peptide nanosheets at pH 7 and 6 with identical peptide content demonstrates that surface charge may be an important mediator in the final assembly morphology.

Surfaced Coated Gold Particles and CMP Sheets and Tubes

In an attempt to correlate the surface charge observed through zeta potential with the topology of the nanosheets and tubes, a series of experiments were conducted with cationic (15 nm amine functional) and anionic (15 nm carboxylate functional) gold nanoparticles. The anionic gold nanoparticles should selectively adsorb onto the positively charged surfaces of the peptide sheets and tubes, while the cationic particles should experience unfavorable repulsion from the structures and would therefore not adsorb onto the surfaces. However, it was observed that both types of gold nanoparticles displayed an affinity for the peptide structures, and, at higher concentration, the gold particles were found to degrade the structures significantly. It seems likely that the charge distributions on the particles interfered with the electrostatic interactions holding the assembled structures together resulting in degradation.

pH-Controlled Mediation Between Two Multicomponent Peptide Assemblies

Knowing that R6P6 assembles into defined sheet structures at pH 6 and tube structures at pH 8, one might control the interconversion between the two structures via pH changes of the assembly medium. Using HCl and NaOH, titration experiments were performed where sheets at pH 6 were titrated to pH 8 and vice versa. After one week of incubation the structures had transitioned to reflect the preferred assembly morphology for the final pH condition. The experiment demonstrates the successful pH-controlled mediation between two different morphologies.

Biotin-Conjugated R6P6 Peptide

A biotin-conjugated R6P6 peptide was synthesized using a D-biotin-15-amido-4,7,10,13-dioxapentadecyl group (biotin-$PEG_2$-acid) that was selectively placed at the N-terminus connected through a $(PEG)_2$ linker. The biotinylated peptide was incorporated into the R6P6/P6E4 annealing process forming heteromeric triple helices and assembled into sheets and tubes at pH 7 and 8, respectively. The structures appeared indistinguishable from those containing only non-biotin conjugated R6P6. The structures were mixed with Cy3B tagged streptavidin and imaged using optical fluorescence microscopy. Fluorescent structures were observed for both sheet and tube assemblies.

These structures have the ability to be functionalized in a variety of ways including biorthogonal functionalization. It is contemplated that multiple functional groups to decorate the assemblies, such as the tubes, with drug like molecules. One can also use the functional sites to bind larger molecules such as enzymes for catalysis or antibodies for selective binding of antigens.

---

The invention claimed is:

1. A composition comprising a first polypeptide and a second polypeptide, wherein the first polypeptide comprises the amino acid sequence of (Pro-Arg-Gly)$_4$-(Pro-Hyp-Gly)$_6$ (SEQ ID NO: 1); and wherein the second polypeptide comprises the amino acid sequence of (Pro-Hyp-Gly)$_6$-(Glu-Hyp-Gly)$_4$ (SEQ ID NO: 2).

2. A composition comprising a first polypeptide and a second polypeptide, wherein the first polypeptide comprises the amino acid sequence of (Pro-Arg-Gly)$_6$-(Pro-Hyp-Gly)$_6$ (SEQ ID NO: 3); and wherein the second polypeptide comprises the amino acid sequence of (Pro-Hyp-Gly)$_6$-(Glu-Hyp-Gly)$_4$ (SEQ ID NO: 2).

* * * * *